US00PP10611P

United States Patent [19]

Alston

[11] Patent Number: Plant 10,611

[45] Date of Patent: Sep. 22, 1998

[54] MANDEVILLA PLANT NAMED 'PSJAM LP1'

[75] Inventor: Jimmy A. Alston, Hodges, S.C.

[73] Assignee: Geo. W. Park Seed Co.,Inc., Greenwood, S.C.

[21] Appl. No.: 717,872

[22] Filed: Sep. 23, 1996

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 8,479 11/1993 Henny ..... Plt./54.1
P.P. 9,117 4/1995 Christensen ..... Plt./54.1

*Primary Examiner*—James R. Feyrer
*Assistant Examiner*—Kent L. Bell
*Attorney, Agent, or Firm*—Foley & Lardner

[57] ABSTRACT

A new and distinct Mandevilla plant named 'PSJAM LP1', particularly characterized by its light pink flower color, large flower diameter and wide overlapping corolla lobes, floriferous habit, and ease of propagation.

3 Drawing Sheets

1

The present invention comprises a new and distinct cultivar of Mandevilla plant, hereinafter referred to by the cultivar name 'PSJAM LP1'.

'PSJAM LP1' originated from a self-pollination of Mandevilla 'Alice Du Pont'. Mandevilla 'Alice Du Pont' represents the backcross of *M.×amabilis×M. splendens* where *M.×amabilis* is an interspecific hybrid of *M. splendens* X an unknown species of Mandevilla, according to *Hortus Third* (Bailey 1976).

The self-pollination were made by the inventor on a single plant being grown at Hodges, S.C., during the summer of 1993. 'PSJAM LP1' was discovered and selected as one flowering plant within the progeny of the stated parentage by the inventor in Jun. 1994, in greenhouses in Greenwood, S.C..

Asexual propagation of the new cultivar by cuttings as performed b the inventor in Jul. 1994, in Greenwood, S.C., showed the first generation to be true to type. Successive generations of asexual propagation have demonstrated that the combination of characteristics as herein disclosed for 'PSJAM LP1' are firmly fixed and can be successively reproduced asexually.

'PSJAM LP1' has not been observed under all possible environmental conditions. The phenotype may vary significantly with variations in the environment such as temperature, light intensity and day length, without, however, any variation in genotype. The following observations, measurements and comparisons describe plants grown in Greenwood, S.C., under greenhouse conditions which approximate those generally used in commercial practice.

The following traits have been repeatedly and consistently observed and are determined to be basic characteristics of 'PSJAM LP1' which in combination distinguish this Mandevilla as a new and distinct cultivar:

(1) The flowers are large, light pink in color and funnel-form in shape. Flower color darkens slightly after flowers have been open 1–2 days, and the flowers remain on the plant an additional 3–4 days. The throat of the flower is a darker pink.

(2) The corolla lobes are wide and overlapping. They are oblique obovate with an off-center abrupt acuminate apex. The corolla lobe margins are slightly undulate.

(3) The cultivar is highly floriferous with each peduncle producing in excess of 40 individual flowers and having up to 4 flowers open on the same day.

(4) Under greenhouse conditions, the cultivar blooms year round but is in heavy bloom from April through October.

(5) The leaves are oblong to elliptic with an abrupt

2 acuminate point. They are leathery, polished and dark green in color and the cultivar is evergreen.

In comparison with the parent 'Alice DuPont', the new cultivar has a lighter pink flower color, wider corolla lobes that overlap more, and a larger corolla diameter. The latter two features also distinguish the new cultivar from 'White Delight', disclosed in U.S. Plant Pat. No. 8,479. In addition, the flower color of 'PSJAM LP1' is a darker pink compared to the flower color of 'White Delight'.

The accompanying color photographic drawings show typical inflorescence and foliage characteristics of 'PSJAM LP1', with the colors being as accurate as possible with illustrations of this type.

The photograph on sheet 1 is a perspective view of the plant.

The photograph on sheet 2 is a photo of a single flower.

The photograph on sheet 3 is a comparative presentation of flowers of 'Alice Du Pont' (lower right), 'PSJAM LP1' (at top) and 'White Delight' (lower left).

In the following description, color references are made to The Royal Horticultural Colour Chart (RHS). The color values were determined on Jul. 12 and Jul. 15, 1996, between 2:00 and 3:00 p.m. in a greenhouse in Greenwood, S.C., under 6000 foot candles of light intensity.

Classification:

A. *Botanical.*—Progeny from selfing the backcross of *M.×amabilis×M. splendens.*

B. *Commercial.*—Mandevilla.

Description

A. Plant:

*Habit.*—Twining vine; twining counter-clockwise; evergreen.

*Height.*—Has not been observed under conditions conducive to maximum growth but has reached 9 m in the greenhouse.

*Stem color.*—Immature, 144B; mature, 152B.

*Stem texture.*—Pubescent.

*Internode length.*—5–25 cm, with the basal ones being the shortest.

Nodal appendages.—3–5 parted dentate; normally 5; color 144A.

B. Foliage:

*Arrangement.*—Opposite.

*Shape.*—Oblong to elliptic with an abrupt acuminate point and cordate base; dimensions vary from 5–13 cm wide and 14–21 cm long.

*Margin.*—Entire.

*Texture.*—Glabrescent and slightly undulated.

*Color.*—Top of immature leaf, 143A; top of mature leaf 137A; bottom of immature leaf, 148B; bottom of mature leaf, 138B; the mid-rib for both immature and mature leaves is 143C; the petioles of both immature and mature leaves are 144B.

C. Inflorescence:

*Type.*—Racemose; in excess of 40 blooms over its life.

*Peduncle.*—45 cm with flower buds still being produced, color 144B.

*Pedicels.*—1.5–2 cm long, twisted; color 144C.

*Bracts.*—0.6–0.7 cm long, triangular shaped; the basal color is 144B; the tip color is 178C.

*Sepals.*—5 in number, each 0.8–1.1 cm long and 0.3–0.4 wide at the base; exterior color 144C, interior color is 144D, with some tips being 178C.

*Corolla type.*—Funnelform; lobes 5; the lobes are oblique obovate with an off-center abrupt acuminate apex.

*Corolla size* (6 *days old*).—Tube is 0.4 cm in diameter and 1.4–1.6 cm long; throat is 2.8–3.2 cm long, conical, and the opening is 2.4–2.6 cm; the lobes are 5.5–6.3 cm long and 5.2–6.5 cm wide, overall face of corolla is 12–15 cm.

*Corolla color* (*in bud*).—The basal tube is 145B; the junction of tube and throat is 145D; the throat is 65D; the lobes still in the roll are 65B.

*Corolla color* (2 *days old*).—Exterior: the tube is 145B; the junction of the tube and throat is 145D; the throat is 65D; the narrow sides of lobes are 65D and the wide sides 65B. Interior: the color deep in the throat is 5B, transitioning through 54C to 68A at the junction of the throat and lobes; the narrow sides of the lobes are 65C, and the wide sides 65A.

*Corolla color* (5 *days old*).—Exterior: the tube is 145B; the junction of the tube and throat is 150D; the throat is 62D, with white lines running from the tube to the dissection point of the lobes; the narrow sides of the lobes are 62D, and the wide sides are 73D. Interior: the color deep in the throat is 4A, transitioning through 55C to 68B at the junction of the throat and lobes; the narrow sides of the lobes are 65D, and the wide sides 65C;

D. Fruit: no fruit has been observed on the new cultivar.

E. Cold hardiness: the cultivar has not been observed in situations to evaluate its hardiness.

I claim:

1. A new and distinct Mandevilla plant named 'PSJAM LP1', as illustrated and described.

* * * * *

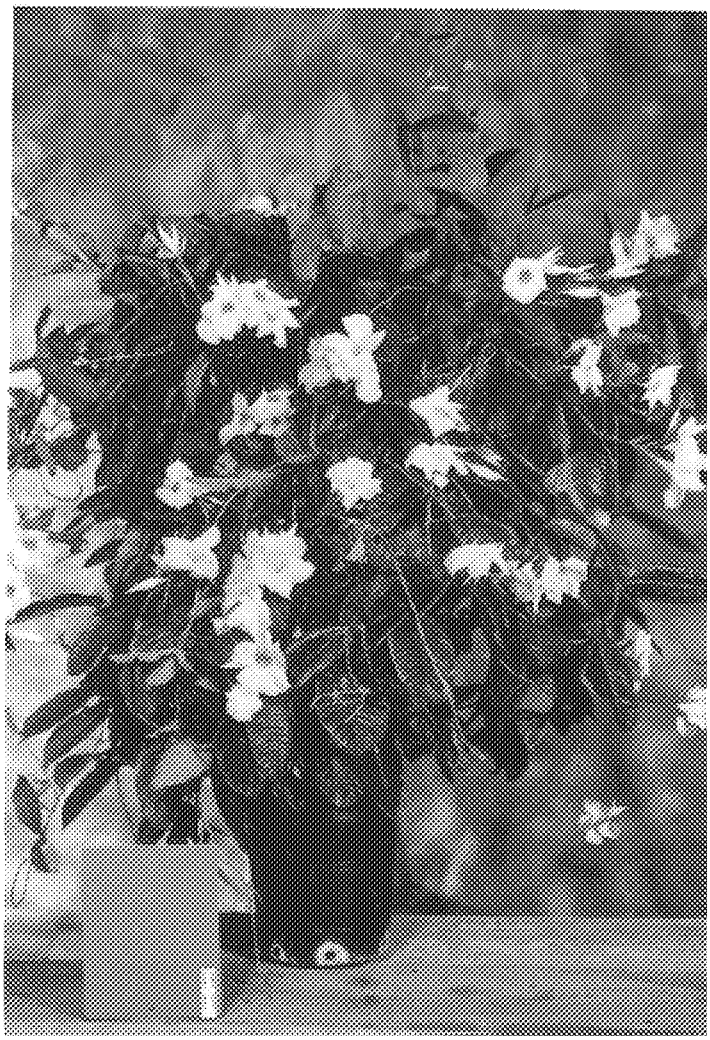

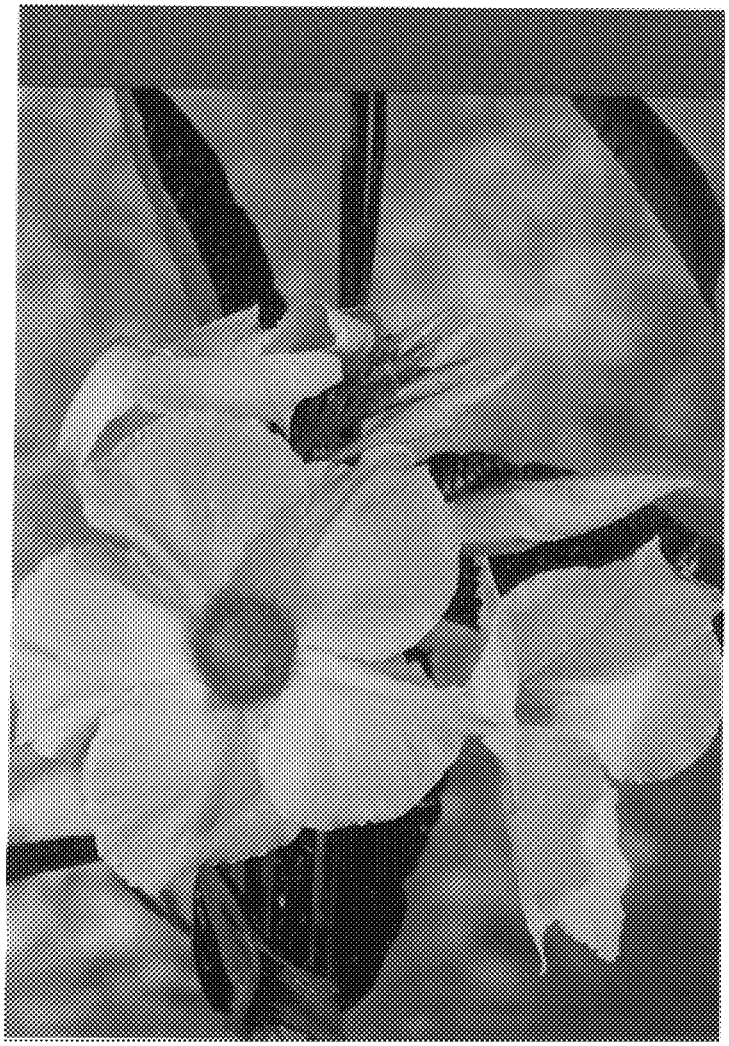

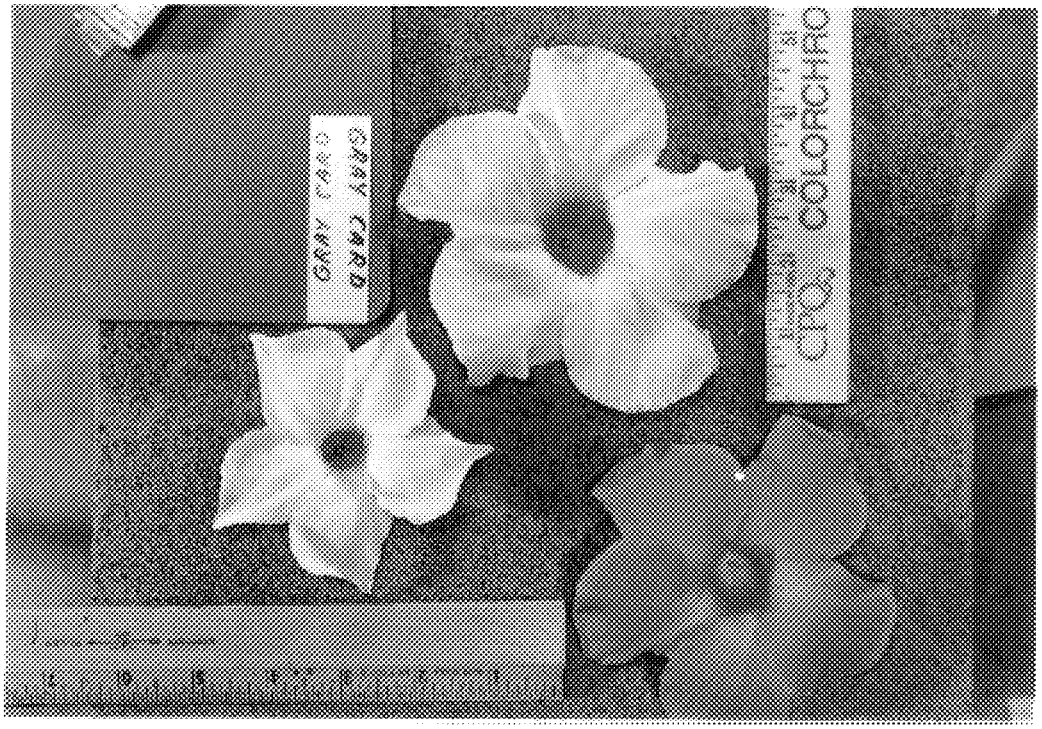
GRAY CARD
GRAY CARD
CROC COLORCHRO